(12) United States Patent
Goudaliez et al.

(10) Patent No.: US 6,890,442 B2
(45) Date of Patent: May 10, 2005

(54) AUTOMATIC HANDLING SYSTEM FOR A BAG SYSTEM

(75) Inventors: Francis Goudaliez, Faches-Thumesnil (FR); Thierry Verpoort, Mouvaux (FR)

(73) Assignee: MacoPharma, Mouvaux (FR)

( * ) Notice: Subject to any disclaimer, the term of this patent is extended or adjusted under 35 U.S.C. 154(b) by 257 days.

(21) Appl. No.: 10/344,302

(22) PCT Filed: Aug. 10, 2001

(86) PCT No.: PCT/FR01/02602

§ 371 (c)(1),
(2), (4) Date: Feb. 7, 2003

(87) PCT Pub. No.: WO02/11788

PCT Pub. Date: Feb. 14, 2002

(65) Prior Publication Data

US 2003/0150508 A1 Aug. 14, 2003

(30) Foreign Application Priority Data

Aug. 10, 2000 (FR) .............................. 00 10534

(51) Int. Cl.$^7$ ............................ B01D 61/00; B65B 3/04; F25D 25/04
(52) U.S. Cl. ..................... 210/645; 210/767; 210/800; 210/384; 210/388; 210/464; 141/10; 198/339.1; 604/6.09; 604/6.15; 604/408; 62/380

(58) Field of Search ................................. 210/645, 646, 210/767, 785, 800, 388, 384, 46; 141/10; 198/456, 339.1, 345.3; 62/380, 78, 67; 604/403–410, 6.09, 6.1, 6.15

(56) References Cited

U.S. PATENT DOCUMENTS

| 4,386,504 A | 6/1983 | Bräutigam .................. 62/380 |
| 5,125,240 A * | 6/1992 | Knippscheer et al. ......... 62/266 |

FOREIGN PATENT DOCUMENTS

| EP | 1048305 A2 | 11/2000 | ............ A61M/1/00 |
| FR | 25881044 | 10/1986 | ........... B65G/1/137 |
| WO | WO94/01193 | 1/1994 | ........... B01B/21/30 |

* cited by examiner

Primary Examiner—W. L. Walker
Assistant Examiner—Krishnan S Menon
(74) Attorney, Agent, or Firm—Baker Botts L.L.P.

(57) ABSTRACT

The invention relates to a method and apparatus for the automatic handling of bag systems in an installation. The method includes the steps of loading at least one bag system having a primary bag containing a body fluid such as blood and a secondary bag into a handling device, wherein the bag system is placed in a position such that no filtering of the body fluid takes place; automatically actuating the handling device so that the bag system is moved to a position wherein filtering occurs; and unloading the bag system from in the handling device when all the filtrate is received in the secondary bag.

27 Claims, 5 Drawing Sheets

AUTOMATIC HANDLING SYSTEM FOR A BAG SYSTEM

CROSS REFERENCE TO RELATED APPLICATIONS

This application is a U.S. National Stage of PCT International Patent Application PCT/FR01/02602 filed Aug. 10, 2001, which claims priority from French Application No. FR 00 10534 dated Aug. 10, 2000.

FIELD OF THE INVENTION

The invention concerns an automatic handling system for at least one bag system in an installation and the said installation.

It applies typically to the case where a fluid, particularly a body fluid, such as blood or a blood component has to be filtered after being collected in the primary bag of a bag system.

Accordingly, the bag system comprises, in addition to the primary bag and connected to it in series by means of tubes, at least one filtration unit and at least one secondary bag intended to collect the filtrate.

BACKGROUND OF THE INVENTION

Filtration by handling, particularly by homogenizing the contents of the primary bag and by turning it manually, the bag system so that the fluid flows from the primary bag to the secondary bag by gravity through the filtration unit is known.

But where a large number of such bag systems have to be handled, this method is very time-consuming.

Furthermore, in the field of the filtration of blood, the time between the collection of blood and its filtration must be monitored accurately to ensure that the filtrate is of high quality.

The manual method described above does not provide for such accurate monitoring, particularly for a large number of bag systems.

In addition, human intervention is a source of errors and does not allow for satisfactory traceability of bag systems and their contents, particularly in terms of the time between collection and filtration and in terms of filtration time.

SUMMARY OF THE INVENTION

The invention is therefore intended to overcome these disadvantages by providing a bag system handling process in an installation which is compact in terms of the number of systems handled, in which human intervention is limited to loading and unloading bag systems before and after filtration respectively and in which bag systems are handled automatically, thus providing for the monitoring of the time between collection and filtration of the fluid.

Accordingly, and according to one aspect, the invention provides a automatic handling process for at least one bag system in an installation; the said bag system comprising at least one primary bag containing a fluid, particularly a body fluid, for example blood or a blood component, at least one filtration unit and at least one secondary bag to collect the filtrate, the said process comprising the following steps:

loading at least one bag system into a handling device, the said bag system being in a position such that filtration of the fluid does not occur;

automatic activation of the handling device so that the bag system is handled to a position in which the fluid flows from the primary bag to the secondary bag passing through the filtration unit, to filter the fluid at a predetermined time;

unloading the bag system in the handling device when the filtrate has been collected in the secondary bag.

According to one embodiment, the process includes, prior to the activation of the handling device, a storage step for the bag system associated with the said device for a predetermined time. For example, the storage step is performed by transferring the bag system associated with the said handling device to a first storage area.

According to one embodiment, the step of activation of the handling device is preceded by a step during which the contents of the bag system are agitated, particularly that of the primary bag. For example, the agitation step may be performed by partial activation of the handling device.

According to one embodiment, the process includes, after the activation of the handling device, a step for storing in the bag system associated with the said device for the time required to filter almost all the fluid. For example, the storage step is performed by transferring the bag system associated with the said handling device to a second storage area.

As a variant, the end of the storage step is controlled by means for detecting the end of filtration.

According to one embodiment, the process also includes one or more steps of identification of the bag system and/or handling device in the installation. For example, the identification step includes the reading and/or recording of data concerning the handling device, the bag system, the contents of the primary bag and the personnel that used the bag system.

As a variant, the data are contained in an electronic device associated with the handling device and/or the bag system, the various steps being controlled as a function of data read during the identification step.

As a variant, an identification step is performed when loading the bag system into the installation to read, in particular, data concerning the contents of the primary bag, the time for the activation of the handling device may be controlled as a function of data read during the identification step and, in particular, according to the sampling time. In addition, the activation of the handling device may also be controlled as a function of the temperature of the fluid to be filtered.

As a variant, an identification step is performed when unloading the bag system, particularly to record data concerning the filtration.

According to one embodiment, a plurality of bag systems are handled in the same handling device; for example, between 10 and 30 bag systems and multiple bag systems are handled in the same installation at the same time. For example, between 500 and 5000 bag systems.

According to a second aspect, the invention provides an installation to implement the process described above, which includes:

a handling device capable of receiving at least one bag system, means of activation capable of activating the handling device from a position in which the fluid in the associated bag system is not filtered to a position in which filtration occurs;

an area for loading the bag system into the handling device;

an area for unloading the bag system associated with the handling device;

an area for activating the handling device in which activation means are provided;

the said installation comprising at least one, main, motorized running track along which the handling device is moved from the loading area to the unloading area, through the activation area, and at least one unit for controlling the movements of the handling device.

According to one variant, the loading and unloading areas are the same.

According to one embodiment, the installation further comprises a first and a second storage areas, in which the bag system associated with the handling device is stored before and after filtration respectively. In this case, the storage areas may be formed by at least one section of the secondary, motorized running track.

According to one embodiment, the installation also comprises an area for the agitation of the contents of the bag system, the said agitation area being fitted with agitation means. For example, the agitation area is identical to the area for the activation of the handling device and the activation means are also agitation means.

According to variants, the installation may also include:
- means for detecting the completion of filtration, the said detection means being connected to the control unit;
- means for identification of the bag system and/or the handling device capable of reading and/or writing data from into the electronic device associated with the said bag system, the said means of identification being connected to the control unit.
- Means for determining the temperature of the fluid to be filtered, the said determination means being connected to the control unit,

BRIEF DESCRIPTION OF THE DRAWINGS

Other purposes and advantages of the invention shall appear during the description below, with reference to the drawings appended.

DETAILED DESCRIPTION OF THE INVENTION

An automatic handling installation according to the invention includes a fixed structure 1 and handling devices 2, in which the bag systems 3 are held.

The handling devices 2 are associated with the fixed structure 1 so that they may be moved along the said structure 1 on the one hand and, activated to filter the fluid on the other hand.

In the embodiment shown in the figures, the handling devices 2 are transferred along the fixed structure 1 overhead, that is the handling devices 2 are suspended from the fixed structure 1 without touching the floor 4 on which the fixed structure 1 is installed.

However, another form of transfer is possible, particularly by placing the handling devices 2 on a conveyor, for example of the endless belt type, or by ensuring that the handling devices 2 can be moved on the ground, by means of wheels for example.

Figure 1:
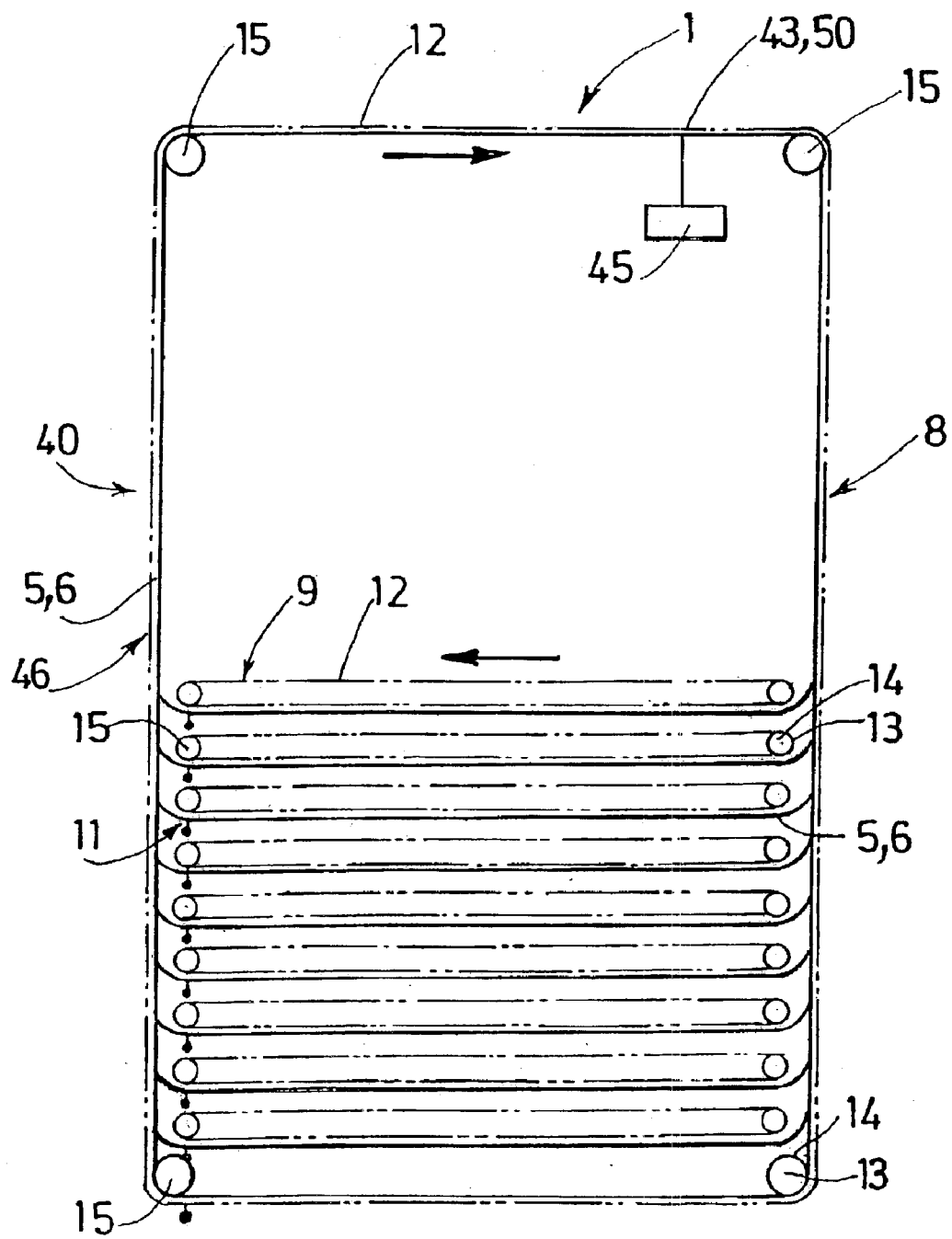
FIG. 1 shows a top view in diagrammatic form of the fixed structure of an automatic handling installation according to the invention, including a main, motorized running track, which is a closed loop and nine sections of secondary, motorized track, which are laid perpendicular to the longest section of the said loop.
Figures 2, 3:
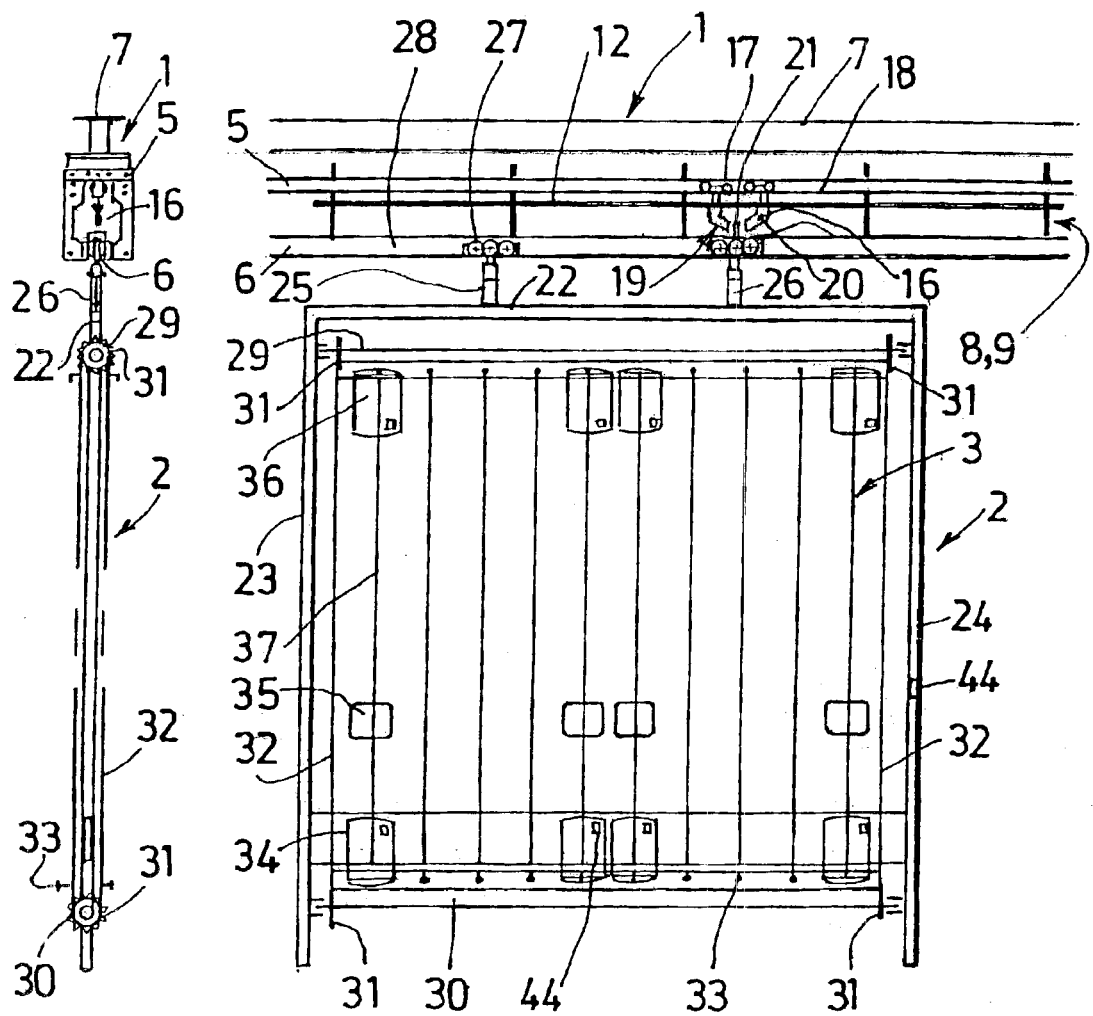
FIG. 2 shows a side view in diagrammatic form of an embodiment of a handling device for ten bag systems, each comprising a primary bag, a filtration unit and a secondary bag, the said device being suspended from the main running track.
FIG. 3 is a profile view of the handling device shown in FIG. 2.

The fixed structure 1 shown in FIGS. 1 and 2 in particular, includes two types of rail, the first of which 5 is installed substantially over the second one 6. The two types of rails 5, 6 are combined at a given distance from each other and are supported by a carrier structure 7. The first type of rail 5 is intended to allow for the driving of handling devices 2, it is therefore known as the "tractor", whereas the second type 6, is intended to support the handling devices 2 suspended from it, and is therefore known as the "carrier".

The rails of the first and second types 5, 6 are, for example, made of steel or similar, so as to be capable of withstanding the forces set up by the weight and movement of the handling devices 2. The rails 5, 6 are either straight or curved and are welded together for example, to form running and drive tracks for the handling devices 2.

In the embodiment shown in FIG. 1, the fixed structure 1 includes a main motorized running track 8, which is a closed loop and nine sections of secondary motorized track 9, which are placed substantially perpendicularly to the longest section of the said loop.

The fixed structure 1 is maintained at a height greater than that of the handling devices 2 by means of posts 10 mounted in the floor 4, so that the said devices 2 can move freely without touching the floor 4.

Although this embodiment is not described specifically here, the fixed structure 1 may include more than one main track 8 and a different number of secondary tracks 9, which may be laid out differently in relation to each other.

In fact, those skilled in the art may adjust the architecture of the fixed structure 1 according to its specific constraints and, in particular, the number of handling devices 2, the nature of the fluids to be filtered, the presence of storage areas and the location for the installation.

In the embodiment described, the handling devices 2 moving on the main track 8 may be diverted by means of a switching system 11 to one of the secondary tracks 9 and vice versa.

Accordingly, a switching system 11 is provided at each intersection between a secondary track 9 and the main track 8; that is, at the end of each of the secondary tracks 9.

The drive of the main running track 8 and secondary tracks 10 in the form of a drive device combined with the tractor rail 5 is described hereinunder.

In the embodiment shown in FIG. 2, this device includes a closed loop cable 12 which is driven in translation in parallel to the tractor rail 5, by means of a motor 13.

Accordingly, the main track 8 comprises a motor-driven pulley 14 and three idler pulleys 15 and each of the secondary tracks 9 comprises a motor-driven pulley 14 and an idler pulley 15. In this case, the movement of the handling devices 2 along the main track 8 is circular whilst that along a secondary track 9 is linear between two points on the main track 8 respectively, in the direction shown by the arrows in FIG. 1.

Mobiles 16 are fixed on to the cable 12 so that they are moved by it. The mobiles 16 comprise wheels 17, which are laid in the groove 18 of the tractor rail 5 so that the mobile 16 is guided during its movements. In addition, the mobile 16 comprises gripping means 19 extending towards the carrier rail 6 and which are capable of engaging an additional part associated with a handling device 2 to transfer the movement of the cable 12 of the said device 2.

As shown in FIG. 2 in particular, the gripping means 19 consist of folding fingers 20 which are activated from a position in which they engage in a dog point 21 of a handling device 2 to a position in which they are disengaged and vice versa.

The gripping means 19 may be activated by a system of cams (not shown) which is supported by a moving part thus enabling the folding fingers 20 to move so that they engage/disengage in dog point 21.

In this example, the switching systems 11 include systems of cams to engage/disengage the dog points 21 of the handling devices 2 of the main running track 8 when changing track.

The number and/or position of the mobiles 16 on the cable 12 is defined particularly depending on the number of handling devices 2 and the type of movements required. For example, the mobiles 16 may be arranged equidistant from each other so that the distance between two successive devices 2 is defined and fixed. This distance may be different depending on the tracks concerned, particularly that between the main track 8 and the secondary tracks 9.

An embodiment of a handling device 2 according to the invention is described below, in reference to FIGS. 2 and 3 in particular.

The handling device 2 comprises a frame made up of three cross members made of steel or similar, for example top 22, left 23 and right 24 cross members respectively, forming three sides of a rectangle.

Two hangers 25, 26 are secured to the outer face of the top cross member 22 to allow for the attachment of the handling device 2 on the carrier rail 6 of the fixed structure 1.

Accordingly, the end of the hangers opposite the upper cross member 22 is fitted with wheels 27 which are engaged in groove 28 of the carrier rail 6 to guide the movements of the handling device 2.

A dog point 21 is installed on one of the hangers 26 near the wheels 27 and projects from the groove 28 of the carrier rail 6, to enable it to engage in the gripping means 19 of the mobile 16, as described above.

In the embodiment, the hanger 26 comprising the dog point 21 is therefore active in terms of the movement of the handling device 2 whilst the other hanger 25 is passive.

Nevertheless a different number of active and/or passive hangers 25,26 may be provided.

Within this framework and associated with the left cross member 23 on the one hand and the right cross member 24 on the other hand, two rotating shafts 29,30 are provided. The two shafts 29,30 are substantially parallel and spaced at a distance D apart.

Each end of the shafts 29,30 is fitted with a toothed wheel 31 capable of being fitted with a chain 32 to control the rotation of each of the two shafts 29,30. Although the embodiment described comprises two chains 32 and four toothed wheels 31, only one chain 32 and two toothed wheels 31 may be provided or another device to control the rotation of the two shafts 29,30 may be devised by those skilled in the art.

Each of the shafts 29,30 comprises means of attachment 33 for the bag systems 3. For example, the bags of a bag systems 3 conventionally include eyelets in which a hook forming the means of attachment 33 may be inserted.

In the embodiment shown, ten means of attachment 33 are provided on each shaft 29,30, opposite each other, so as to be able to associate ten bag systems 3 in each handling device 2.

The bag systems 1 comprise a primary bag containing fluid, particularly a body fluid, for example blood or a blood component, at least one filtration unit 35 and one secondary bag 36 to collect the filtrate, the bags 34,36 and the filtration unit 35 being connected to each other by tubes 37.

In this case, the installation may be a closed circuit with filtration and collection of the filtered fluid being carried out when the handling device 2 is activated.

When loading the bag system 1, the primary bag 34 is associated with the lower shaft 30 and the secondary bag 36 with the top shaft 29 by means of attachment means 33 (see FIG. 2). In this position, filtration of the fluid by gravity does not take place.

In the embodiment shown, the ten bag systems 3 are placed substantially in parallel to each other with their filtration unit 35 between the two shafts 29,30; the space defined between the two shafts 29,30 being empty. However, an endless belt may be provided to support the filtration units 35.

The bag systems 3 may be identical and/or different, in particular, they may include other bags, other filtration units or any other devices required to treat the fluid before and/or after filtration.

In a special example, the primary bag 34 contains whole blood and the filtration unit 35 is capable of eliminating leucocytes. In this case, the bag system 3 may also include a first and a second satellite bags connected in series to the secondary bag. In this embodiment, the filtration is carried out in an installation according to the invention then, after unloading the bag system 3, the secondary bag 36 is centrifuged to collect the red blood cell concentrate and the plasma in the first and secondary satellite bags respectively.

Depending on the nature and/or the geometry of the bag systems 3 to be installed in the handling devices 2, the distance D may be adjustable, in particular, by providing adjustment means capable of having shafts 29 or 30 slide in relation to each other.

The operation of such a handling device 2 using a first jack 38 and a second jack 39, of the pneumatic or rack and pinion type for example (see FIG. 7a to 7c) is described below.

The jacks 38,39 are installed in an area of the installation, known as the activation area 40 of the handling device 2, in which the gripping means 19 are disengaged so that the said device 3 cannot be moved.

The chains 32 are fitted with means forming sockets for the rod 42 of the jacks 38,39, for example in the form of stops 41a, 41b, which project from the handling device 2. There are, for example, two stops 41a, 41b and they are installed on one of the chains 32, at a distance approximately equal to D.

Figures 7A, 7B, 7C:
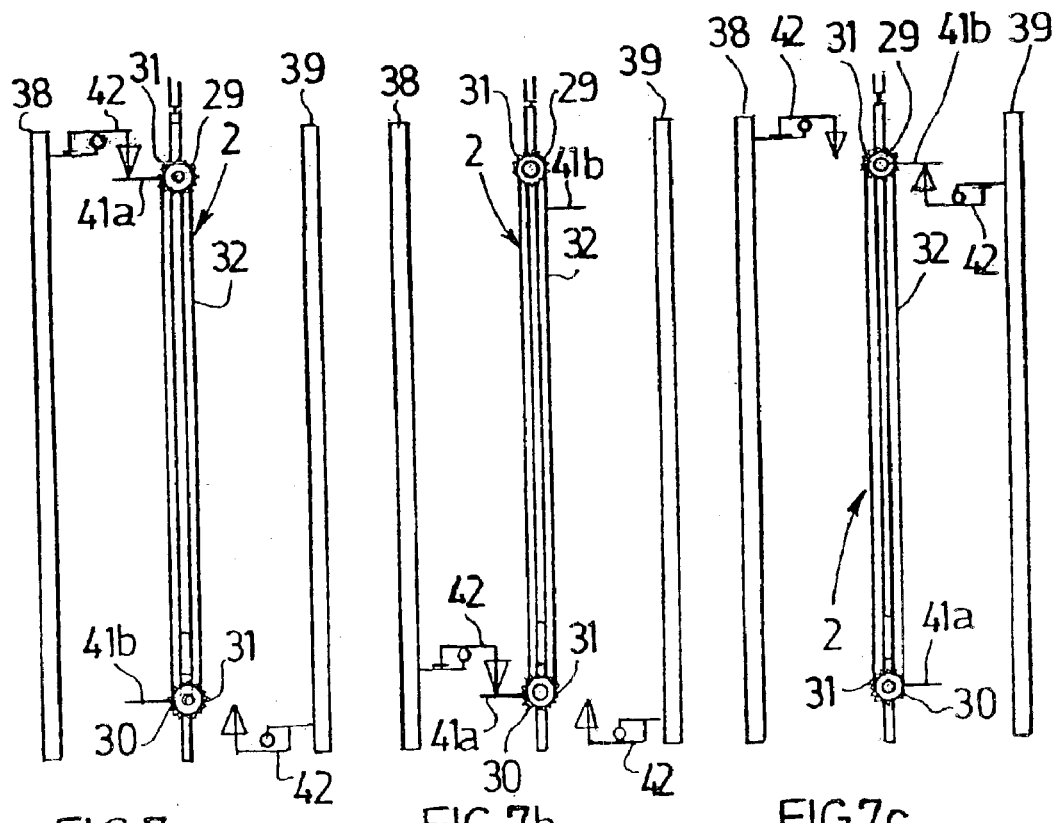
FIGS. 7a to 7c show side views in diagrammatic form of an embodiment of activation means capable of activating a handling device according to FIG. 2, from a position in which the fluid in the associated bag system is not filtered to a position in which the fluid is filtered, and three steps of this operation.

FIG. 7a shows the handling device 2 in a position in which the fluid is not filtered. In this position, the primary bag 34 is installed above the secondary bag 36 so that the fluid cannot flow between the two bags 34, 36 by gravity.

To activate the handling device 2, the first jack 38 engages on the top stop 41a to move it over a distance of D, the second jack 39 being disengaged.

During this movement, the stop 41a drives the chain 32 and therefore the two shafts 29, 30 through toothed wheels 31 and therefore the associated bag systems 3. The bag systems 3 are now in a position (FIG. 7b) in which the primary bag 34 is above the secondary bag 36 so that the fluid flows and is therefore filtered by gravity.

In a third step, the first jack 38 is disengaged and the second jack 39 is engaged on the second stop 41b. The first jack 38 is moved towards its initial position whilst the second jack 39 is moved to complete the turning of the bag systems 3 in the handling device 2 (FIG. 7c).

A process using an installation according to the installation is described below.

In the example of use described, the motor 13 which drives the cable 12 of the main track 8 runs continuously so that the handling devices 2 which are engaged above it on mobiles 16 move at a constant speed.

However, this movement may be made at a non-constant speed and/or discontinuously by adjusting the speed of the motor 13.

The use is described for a single handling device 2 related to the installation; it is understood that these steps are performed continuously and in parallel for a large number of handling devices 2 so that the installation provides for the processing of 500 to 5000 bag systems 3 simultaneously.

In a first step, the bag systems 3 are loaded into a handling device 2.

Accordingly, an area 43 is provided in the installation to which the personnel responsible for loading has easy access and in which the handling device 2 to be loaded cannot be moved.

Such a loading area 43 may consist of a section of non motorized track on which the handling device 2 moving on the main track 8 is diverted. The mobile 16 which moves the handling device 2 on the main track 8 is disengaged by means of a switching system 11.

The operator can then load the fixed handling device 2 with the bag systems 3 containing the fluid to be filtered, the said systems 3 being placed in a position in which filtration does not occur.

During this loading, a step to identify the bag systems 3 and/or the handling device 2 is performed.

Accordingly, the bag systems 3 and/or the handling device 2 may be fitted with an electronic device 44 capable of recording and/or generating data to monitor the bag system 3 and/or its contents.

The operator reads the data in the electronic devices 44 using a scanning device, the said scanning device being connected to a control unit 45 of the installation, consisting of an electronic controller for example.

Depending on the data read, the control unit 45 calculates the time and/or place of storage for the handling device 2 in the installation.

In particular, the data read concerning, in particular, the contents of the primary bag 34 and the time at which the primary bag was filled, that is the time the sample of fluid was taken. In fact, it is well known that a blood component should be filtered within a pre-determined time span after being collected.

Once loading and identification have been completed, the operator moves, manually for example, the handling device 2 to a second switching system 11, which allows the said device 2 to be returned to the main track 8 by engaging a mobile 16 on the dog point 21 to move it along the said track 8.

Figure 4:
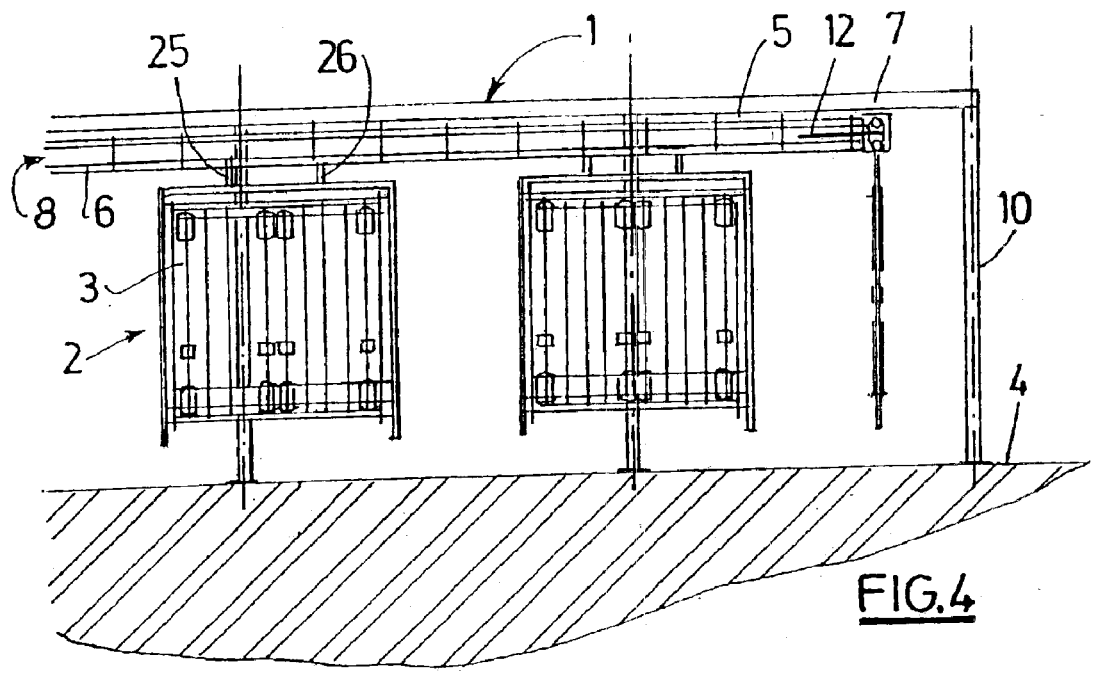
FIG. 4 shows a side view in diagrammatic form of two handling devices similar to those shown in FIG. 2 and which move together, one behind the other, on the main running track.

In this case, the handling device 2 is moved along the main track 8 towards the storage area 9 which has been determined by the control unit 45 (see FIG. 4).

When the handling device 2 arrives on the switching system 11 of the storage area 9 selected, the control unit 45 activates the said system 11 so that the handling device 2 is diverted to the secondary track 9 and the mobile 16 that moves it is disengaged.

Figure 5:
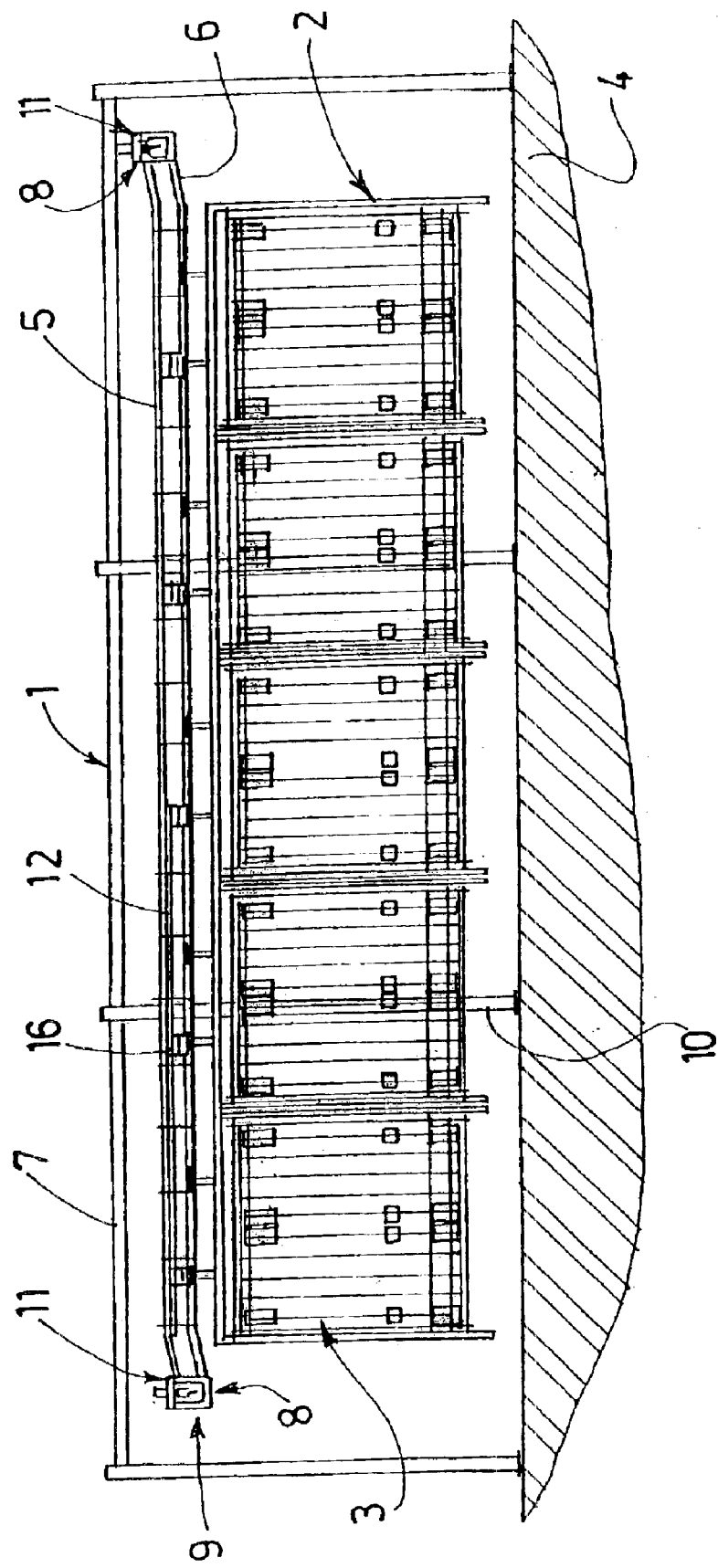
FIG. 5 shows a side view in diagrammatic form of five handling devices similar to that shown in FIG. 2, on a section of secondary track forming the storage area.

The handling device 2 is now on the secondary track 9, with other handling devices 2, waiting to be activated (see FIG. 5).

It is understood that the control unit 45 adjusts the flow of handling devices 2 on the secondary tracks 9 so that they are disengaged in chronological order of activation.

The activation device 2 is also moved on the secondary storage track 9 by the mobiles 16 which engage and disengage on the dog point 21.

In a special example, the motor 13 that drives the cable 12 of the secondary tracks 9 is activated discontinuously by the control unit 45 and according to storage/removal from storage requirements.

The removal of storage of the handling device 2 is controlled by the control unit 45, particularly according to the time elapsed since sampling.

As a variant, means for measuring the temperature of the fluid (not shown) are provided in the storage area 9 to trigger removal from storage when the temperature of the fluid is within the optimum operating range of the filtration unit 35.

The measuring means are, for example, of the infrared type and the optimum operating range is typically between 18° C. and 22° C. for the filtration of the whole blood.

During the removal from storage step, the handling device 2 is moved to a switching system 11 which enables the said device 2 to be returned to the main track 8 by engaging a mobile 16 above it to move it to an agitation area 46.

Figure 6:
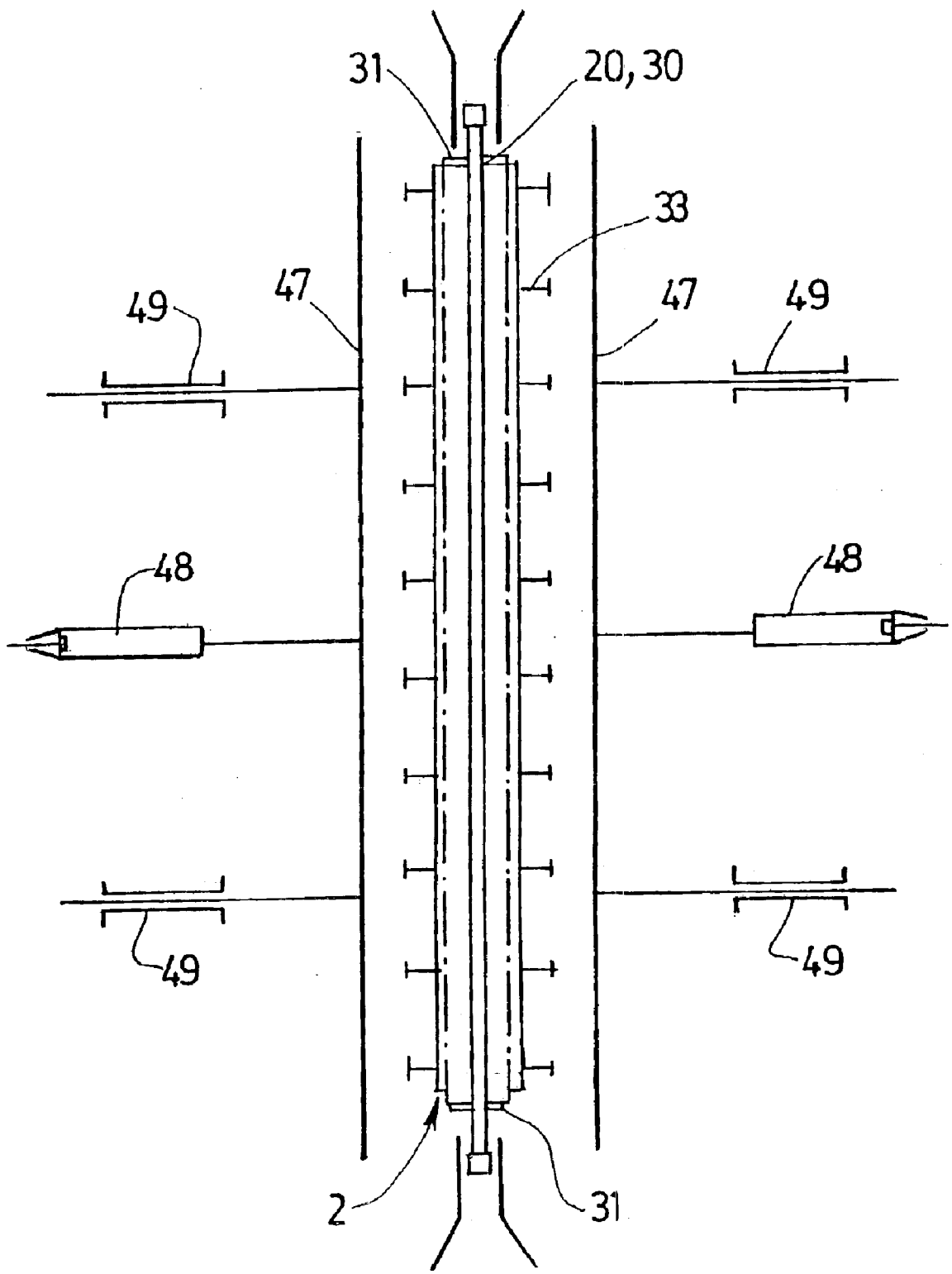
FIG. 6 shows a top view in diagrammatic form of an embodiment of the means to agitate the contents of the bag system associated with a handling device according to FIG. 2.

In a first variant, the bag systems are agitated by a system of plates 47 operated by jacks 48 so that the bags 34, 36 are pressed alternatively (see FIG. 6).

In this variant, the handling device 2 is immobilized for example on a section of track parallel to the main track 8 and connected to it by switching systems 11. Immobilization is carried out opposite to the plates 47 then the jacks 48 are activated so that the plates 47 are moved in translation with an oscillating movement, guide means 49 being provided to assist such movements. The plates 47 therefore press the bag systems 3, and particularly the primary bags 34, to put the various components of the fluid back into suspension.

The handling device 2 is then moved to an activation area 40 on the main track 8.

In a second variant, the agitation area 46 and the activation area 40 are the same, with agitation being performed by partial activation of the handling device 2.

In the activation area 40, the device 2 is immobilized for example on a section of track parallel to the main track 8 and connected to it by switching systems 11. Immobilization is Carried out opposite to the first and second jacks 38, 39, which activate it as described above.

In the second variant and prior to complete activation, partial and alternating activation is performed to return the components of the fluid into suspension.

Accordingly, the jacks 38, 39 are of the double-acting type to ensure that the bag systems 3 are turned over partially several times, for example between the initial position and half the distance D, and vice versa.

Such partial activation should be performed over a distance so that the fluid does not enter the filtration unit 35 to avoid the start of filtration.

Once agitation and activation are complete, the handling device 2 is moved along the main track 8 to a secondary track 9 to be stored for the time required for the filtration of almost all the fluid.

Where the filtration time is short and/or the time for movement from the activation area 40 to the unloading area 50 is long, the second storage area may not be provided so that filtration takes place along the main track 8.

When the second storage area is provided, it may be fitted with means to detect the completion of filtration (not shown) which since they are connected to the control unit 45, control the exit of the device 2 from the second storage area. The device 2 is then moved along the main track 8 towards the unloading area 50.

In addition, these determination means may be used to detect any problems during filtration, for example filtration that is too quick or too slow.

These determination means are, for example, of the optical type to detect the presence or absence of fluid in the tube 37 or to measure the thickness of bags 34, 36.

Once filtration is complete, the handling device 2 is moved to the unloading area 50 which, in the embodiment shown in the figures, is the same as the loading area 43.

The operator removes the bag systems 3 from the handling device 2 so that the filtered fluid may be used in a conventional way.

During this unloading step, the operator may also write data into the electronic device 44 of the bag systems 3 and/or the handling device 2.

These different steps consisting in reading writing data ensure the traceability of the fluids treated, in particular, all data may be stored in a central unit connected to the control unit 45 of the installation to retain a trace of all operations performed.

In addition, the succession of operating steps and the management of the flow of handling devices 2 are performed automatically by the control unit 45 as a function of such data.

What is claimed is:

1. A method for handling at least one bag system in an installation the bag system having at least one primary bag containing a fluid, at least one filtration unit and at least one secondary bag to collect filtrate, said method comprising the steps of:
   (a) loading at least one bag system into a handling device in a loading section of the installation, the at least one bag system being in a position such that filtration does not occur;
   (b) moving the handling device in an activation section of the installation using a pair of jacks disposed adjacent to the handling device so that the bag system is moved to a position in which the fluid flows from the primary bag to the secondary bag passing through the filtration unit to filter the fluid at a pre-determined time;
   (c) moving the handling device through the installation from the loading section, through the activation section to an unloading section using at least one main motorized track and at least one unit for controlling the movement of the handling device in the installation; and
   (d) unloading the bag system from the handling device in the unloading section of the installation when the filtrate has been collected in a the secondary bag.

2. A method according to claim 1, further comprising the step of storing the bag system in the handling device for a pre-determined time prior to performing step (b).

3. A method according to claim 2, wherein the storage step is performed by transferring the at least one bag system to a first storage area.

4. A method according to claim 1, wherein step (b) is preceded by a step of agitating the at least one bag system.

5. A method according to claim 4, wherein the agitation step is performed by partial activation of the handling device.

6. A method according to claim 1, further comprising the step of storing the at least one bag system for a period of time required to filter almost all the fluid subsequent to performance of step (b).

7. A method according to claim 6, wherein the storage step is performed by transferring the at least one bag system from a first storage section of the installation to a second storage section of the installation.

8. A method according to claim 6 wherein the end of the storage step is controlled by means for detecting the end of filtration.

9. A method according to claim 1, further comprising one or more steps of identifying the at least one bag system and/or handling device.

10. A method according to claim 9, wherein the identification step includes the reading and/or recording of data relating to the handling device, the at least one bag system, contents of the primary bag and the personnel that used the at least one bag system.

11. A method according to claim 10, wherein the data are stored in an electronic device associated with the handling device and/or the at least one bag system.

12. A method according to claims 10 wherein the series of different steps is controlled as a function of the data read during the identification step.

13. A method according to claims 10 wherein an identification step is performed during the loading of the at least one bag system into the handling device to read the data concerning the contents of the primary bag.

14. A method according to claim 13, wherein the time at which step (b) is performed is controlled as a function of the time that the fluid is collected.

15. A method according to claim 14, wherein the time at which step (b) is performed is also controlled as a function of the temperature of the fluid to be filtered.

16. A method according to claim 9 wherein an identification step is performed during unloading of the bag system to record data relating to filtration.

17. A method according to claim 1, wherein 10 to 30 bag systems are loaded in the same handling device.

18. A method according to claim 1, wherein 500 to 5000 bag systems are loaded in the same handling device.

19. An installation for handling at least one bag system having at least one primary bag containing a fluid, at least one filtration unit and at least one secondary bag to collect filtrate, the installation comprising:
   (a) a handling device capable of handling at least one bag system;
   (b) a pair of jacks disposed adjacent to the handling device which move the handling device from a position in which the fluid in the associated bag system is not filtered to a position in which filtration occurs;

(c) a loading section in which the handling device is immobile for associating the at least one bag system with the handling device;

(d) an unloading section in which the handling device is immobile for removing the bag system associated with the handling device;

(e) an activation section in which the handling device is moved by the pair of jacks; and (f) wherein the installation comprises at least one main motorized running track along which the handling device is moved from the loading section to the unloading section via the activation section and;

(g) wherein the installation comprises at least one unit for controlling the movements of the handling device in the installation.

20. An installation according to claim 19, wherein the loading section and the unloading section are in the same location.

21. An installation according to claim 19, further comprising first and second storage sections in which the at least one bag system associated with the handling device is stored before and after filtration respectively.

22. An installation according to claim 21, wherein the storage areas comprise at least one section of secondary, motorized running track.

23. An installation according to claim 19, further comprising means for agitating the contents of the at least one bag system.

24. An installation according to claim 23, wherein the agitation means includes the pair of jacks.

25. An installation according to claim 19, further comprising means for detecting the completion of filtration, said detection means being connected to a control unit.

26. An installation according to claim 19, further comprising means to identify the at least one bag system and/or the handling device capable of reading and/or writing data from/into an electronic device associated with the at least one bag system and/or handling system, said means of identification being connected to the control unit.

27. An installation according to claim 19, further comprising means for measuring the temperature of the fluid to be filtered, said measuring means being connected to the control unit.

* * * * *